(12) United States Patent
Wang et al.

(10) Patent No.: US 10,578,533 B2
(45) Date of Patent: Mar. 3, 2020

(54) SPECIMEN FOR EVALUATING PRESSURE PULSE CAVITATION IN ROCK FORMATIONS

(71) Applicant: UT-Battelle, LLC, Oak Ridge, TN (US)

(72) Inventors: Jy-An John Wang, Oak Ridge, TN (US); Hong Wang, Oak Ridge, TN (US); Fei Ren, Philadelphia, PA (US); Thomas S. Cox, Oak Ridge, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 250 days.

(21) Appl. No.: 15/291,294

(22) Filed: Oct. 12, 2016

(65) Prior Publication Data

US 2017/0067808 A1    Mar. 9, 2017

Related U.S. Application Data

(62) Division of application No. 14/224,414, filed on Mar. 25, 2014, now Pat. No. 9,500,068.

(51) Int. Cl.
| | |
|---|---|
| *G01N 3/56* | (2006.01) |
| *F17D 1/08* | (2006.01) |
| *H05B 7/18* | (2006.01) |
| *E21B 43/26* | (2006.01) |
| *E21B 49/00* | (2006.01) |
| *B23K 26/122* | (2014.01) |

(Continued)

(52) U.S. Cl.
CPC ........... *G01N 3/567* (2013.01); *B23K 26/122* (2013.01); *E21B 43/26* (2013.01); *E21B 49/006* (2013.01); *F17D 1/08* (2013.01);

*G01N 29/2418* (2013.01); *G01N 33/2823* (2013.01); *H05B 7/18* (2013.01); *G01N 2203/0055* (2013.01); *Y10T 137/0391* (2015.04)

(58) Field of Classification Search
CPC ........ G01N 3/567; B23K 26/122; E21B 43/26
USPC ................................................. 73/865
See application file for complete search history.

(56) References Cited

U.S. PATENT DOCUMENTS

| | | |
|---|---|---|
| 4,787,446 A | 11/1988 | Howell et al. |
| 6,419,022 B1 | 7/2002 | Jernigan et al. |

(Continued)

OTHER PUBLICATIONS

D. Pixton and D. Hall, "Advanced Mud Hammer System,".

(Continued)

*Primary Examiner* — Tarun Sinha
(74) *Attorney, Agent, or Firm* — Warner Norcross + Judd LLP

(57) ABSTRACT

An apparatus 300 for simulating a pulsed pressure induced cavitation technique (PPCT) from a pressurized working fluid (F) provides laboratory research and development for enhanced geothermal systems (EGS), oil, and gas wells. A pump 304 is configured to deliver a pressurized working fluid (F) to a control valve 306, which produces a pulsed pressure wave in a test chamber 308. The pulsed pressure wave parameters are defined by the pump 304 pressure and control valve 306 cycle rate. When a working fluid (F) and a rock specimen 312 are included in the apparatus, the pulsed pressure wave causes cavitation to occur at the surface of the specimen 312, thus initiating an extensive network of fracturing surfaces and micro fissures, which are examined by researchers.

10 Claims, 12 Drawing Sheets

(51) Int. Cl.
    *G01N 29/24*    (2006.01)
    *G01N 33/28*    (2006.01)

(56) References Cited

U.S. PATENT DOCUMENTS

| | | | |
|---|---|---|---|
| 6,588,283 B2 * | 7/2003 | Wang | G01N 3/22 |
| | | | 73/799 |
| 7,921,876 B2 | 4/2011 | Wright et al. | |
| 2007/0063513 A1 * | 3/2007 | Boyd | E21B 17/04 |
| | | | 285/355 |
| 2008/0145179 A1 * | 6/2008 | Amann | F16B 17/006 |
| | | | 411/378 |
| 2009/0071658 A1 * | 3/2009 | Reid | E21B 23/006 |
| | | | 166/373 |
| 2011/0056695 A1 | 3/2011 | Downton | |
| 2011/0232917 A1 | 9/2011 | Skinner et al. | |
| 2012/0043092 A1 | 2/2012 | Arizmendi, Jr. et al. | |
| 2012/0103595 A1 | 5/2012 | Hall et al. | |

OTHER PUBLICATIONS

Jy-An John Wang, "Oak Ridge National Laboratory Spiral Notch Torsion Test (SNTT) System," Practical Failure Analysis, 2003, pp. 11-15, vol. 3(4).
Jy-An John Wang, et al., "A New Test Method for Determining the Fracture Toughness of Concrete Materials," Cement and Concrete Research, 2010, pp. 497-499, vol. 40.

* cited by examiner

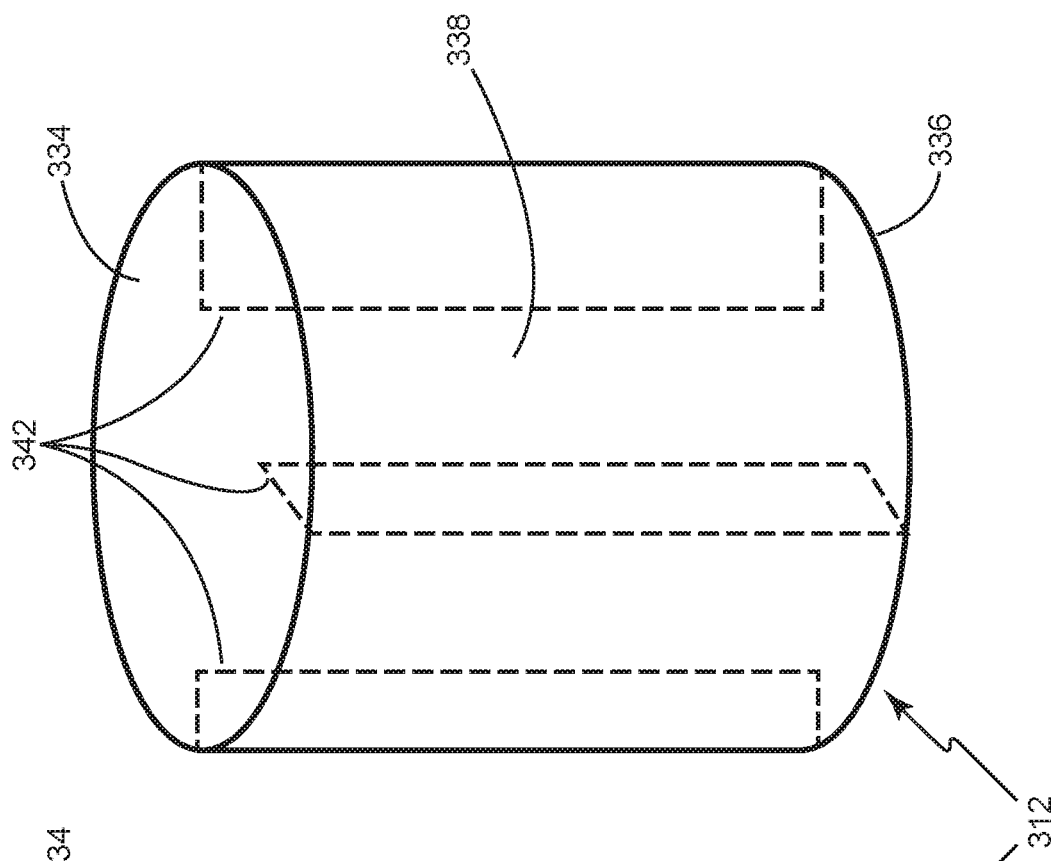
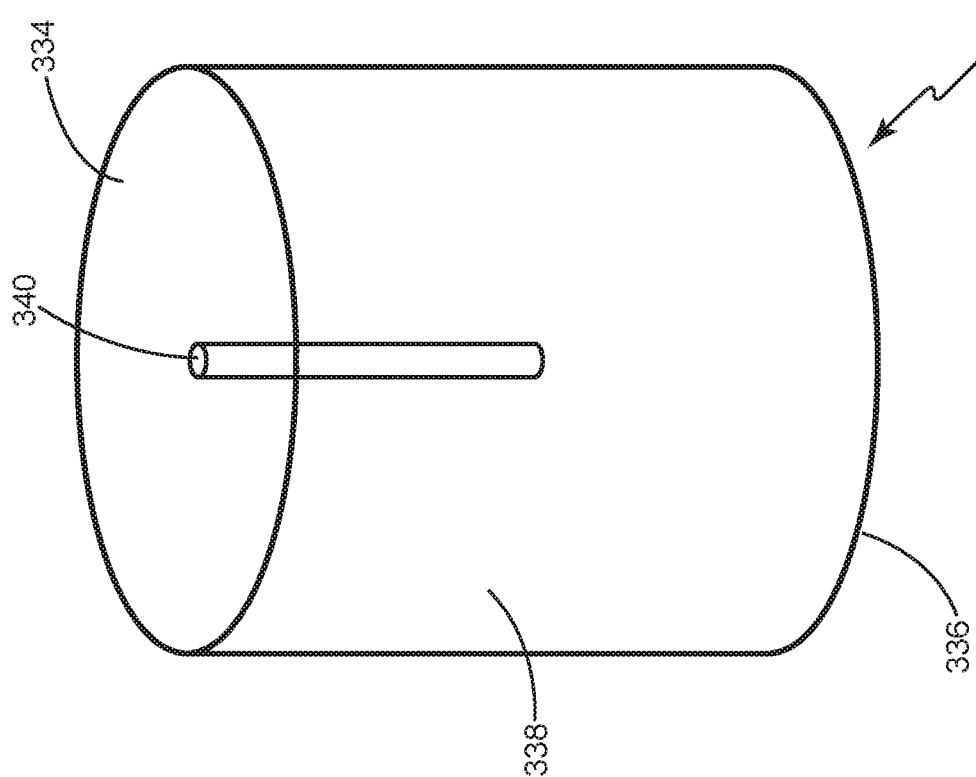

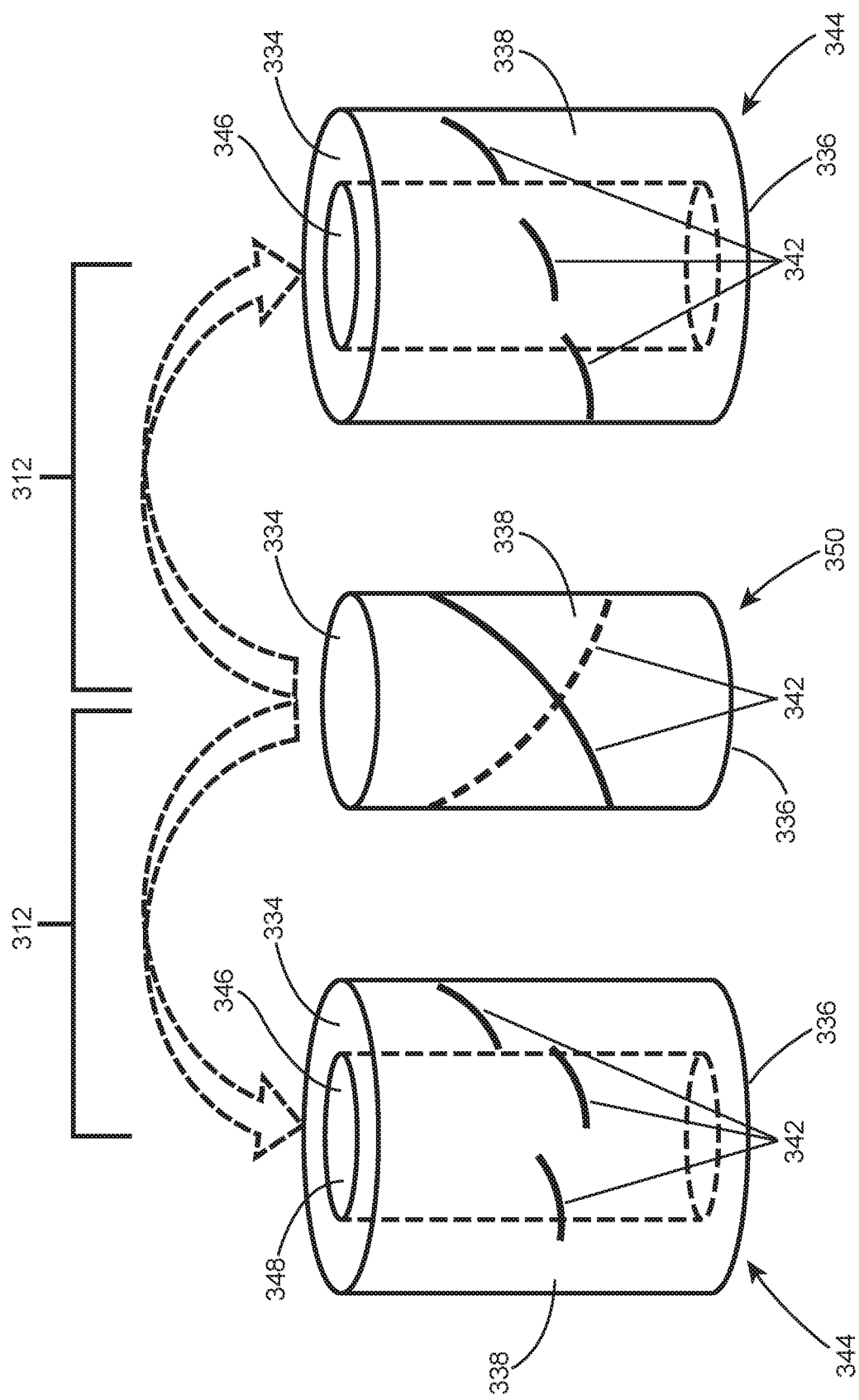

SPECIMEN FOR EVALUATING PRESSURE PULSE CAVITATION IN ROCK FORMATIONS

CROSS-REFERENCE TO RELATED APPLICATIONS

This patent application is a divisional of, and claims priority to, copending U.S. application Ser. No. 14/224,414 filed on 25 Mar. 2014 and entitled, "CAVITATION-BASED HYDRO-FRACTURING SIMULATOR" the entire content of which is included herein as if included at length. This patent application is related to U.S. application Ser. No. 14/224,367 filed on 25 Mar. 2014 and entitled, "A CAVITATION-BASED HYDRO-FRACTURING TECHNIQUE FOR GEOTHERMAL RESERVOIR STIMULATION", and U.S. patent application Ser. No. 12/945,252 filed on 12 Nov. 2010 and entitled, "REPETITIVE PRESSURE-PULSE APPARATUS AND METHOD FOR CAVITATION DAMAGE RESEARCH" the entire contents of which are included herein by reference as if included at length.

STATEMENT REGARDING FEDERALLY SPONSORED RESEARCH AND DEVELOPMENT

This invention was made with government support under Contract No. DE-AC05-00OR22725 awarded by the U.S. Department of Energy. The government has certain rights in the invention.

THE NAMES OF THE PARTIES TO A JOINT RESEARCH AGREEMENT

None.

BACKGROUND OF THE INVENTION

1. Field of the Invention

The present disclosure relates to enhanced geothermal system (EGS) production and particularly to apparatuses and methods for simulating a cavitation-based hydro-fracturing technique.

2. Description of the Related Art

Geothermal energy is an important part of the nation's renewable energy initiative. FIG. 1 illustrates a simplified schematic of a geothermal plant that generates electricity for the electrical grid. A working fluid (F) such as water is transferred with a pump 100 down into the hot rock formations through an injection well 102, where it absorbs heat energy from the fractured rock formation. The heated working fluid (F) is then pumped to an energy conversion plant 104 through a production well 106. Depending on the fluid's (F) temperature, it may directly be used to power a turbine or may be used to heat a secondary working fluid, which, in turn, is used to power a turbine. The turbine is coupled to a generator through a common shaft (not shown), to generate electricity for the electrical grid 108. The cooled working fluid (F) is then injected with the pump 100 back into the hot rock geothermal reservoir through the injection well 102 to sustain the process. Geothermal energy generation is considered a green technology, because little or no greenhouse gases are emitted into the atmosphere and the energy source is renewable.

An Enhanced Geothermal System (EGS) is a man-made reservoir, created where there is sufficient underground hot rock but insufficient or little natural permeability or working fluid (F) saturation in the rock. EGS expands the geothermal energy domain into much deeper rock deposits by exploiting natural and artificial fracture systems/networks within the rock mass. Maintaining and/or creating such fracture networks in complicated geological environments are critical to the successful development and long-term sustainability of the EGS. The EGS targets a huge energy source that amounts to 500 GWe in the western U.S. and 16,000 GWe in the entire U.S. Several demonstration projects are undergoing in the U.S. to validate different reservoir stimulation techniques. The ultimate reservoir will have a flow rate of 60 kg/s, a lifetime of 30 years along the drilling systems down to 10,000 meters deep at 374 Degrees Celsius.

EGS reservoir stimulation technologies currently are adapted from the oil and natural gas industry including various hydrofracking methods with or without chemical additives. A potential drawback of using hydrofracking techniques is the lack of effective control in the creation of large fractures, which could result in by-pass of targeted fracture network or even fault movement in the rock formation. The loss of hydraulic medium can reduce heat exchange efficiency and increase the cost of the development of EGS. The use of chemicals along with the unpredictable fault movement may also adversely impact the environment.

Cavitation is the process of the formation of vapors, voids, or bubbles due to pressure changes in a liquid flow as schematically illustrated in FIG. 2. The pressure wave propagation 200, and eventual collapse of the bubbles 202 can cause local pressure changes in the working fluid (F), which can be transmitted to a target rock surface 204 either in the form of a shock wave 206, or by micro-jets 208, depending on the bubble to surface distance. Pressure greater than 100,000 psi has been measured in a shock wave 206 resonating from cavitating bubbles 202. It is generally understood that the cycle of formation and collapse of the bubbles that occurs, often at a high frequency, can generate dynamic stress on the surfaces of objects. Ultimately, the dynamic stress can contribute to the fatigue of the target surface, including micro-cracks that form and coalesce on the surface 204, eventually leading to material removal known as cavitation damage.

The operations of geothermal, oil and natural gas wells are expensive endeavors. Well site development and production activities involve vast capital investments in land and equipment as well as the support of highly specialized personnel. Due to these large investments, opportunities for in-situ research and development efforts in the geothermal, oil and natural gas industries may not be cost prohibitive.

What are needed are apparatuses and methods for simulating a pulse-pressure cavitation technique (PPCT) in a laboratory environment.

BRIEF SUMMARY OF THE INVENTION

Disclosed are several examples of apparatuses and methods for simulating a pulse-pressure cavitation technique (PPCT) in a laboratory environment.

Described in detail below is an apparatus for generating a pulsed pressure induced cavitation technique (PPCT) from a pressurized working fluid to simulate the hydrofracturing of a specimen when a working fluid and specimen are installed. In the apparatus, a pump is fluidly coupled to, and disposed downstream of, a reservoir and fluidly coupled to, and disposed downstream of, a control valve having an open position and a closed position, the pump capable of raising the pressure of a working fluid at the control valve. Also included is a test chamber for holding a specimen when a specimen is installed in the apparatus. The test chamber is fluidly coupled to, and disposed downstream of, the control valve and receives a working fluid from the control valve when the control valve is in the open position. Also included is a pressure regulator that is fluidly coupled to, and disposed downstream of, the test chamber and fluidly coupled to, and disposed upstream of, the reservoir. When the control valve is in the open position, it causes a working fluid to flow into the test chamber as a pressure pulse, causing cavitation to occur in a working fluid adjacent to a specimen when a specimen and a working fluid are installed in the apparatus. Other features and examples will be described in greater detail.

Also described in detail below is an article or specimen for receiving a pulsed pressure induced cavitation technique (PPCT) from a pressurized working fluid as generated by a test apparatus. The specimen includes a shell body defined by a circular top surface, a circular bottom surface and a convex side surface joining the top and bottom. Also included in the shell body is an aperture defined by an opening in the top surface and an opening in the bottom surface. Also included is a core body defined by a top surface, a bottom surface and a convex side surface joining the top surface and bottom surface. The core body is disposed inside of the aperture in the shell body and the shell body and core body are made of rock materials. Other features and examples will be described in greater detail.

BRIEF DESCRIPTION OF THE SEVERAL VIEWS OF THE DRAWINGS

The apparatus and method may be better understood with reference to the following non-limiting and non-exhaustive drawings and description. The components in the figures are not necessarily to scale, emphasis instead being placed upon illustrating principles. In the figures, like referenced numerals may refer to like parts throughout the different figures unless otherwise specified.

FIG. 11 is an illustration of an exemplary specimen.

FIG. 12 is an illustration of another exemplary specimen.

FIG. 13 is an illustration of an exemplary specimen shell.

FIG. 14 is an illustration of an exemplary specimen core for use with the shells of FIGS. 13 and 15.

FIG. 15 is an illustration of another exemplary specimen shell.

DETAILED DESCRIPTION OF THE INVENTION

Figure 1:
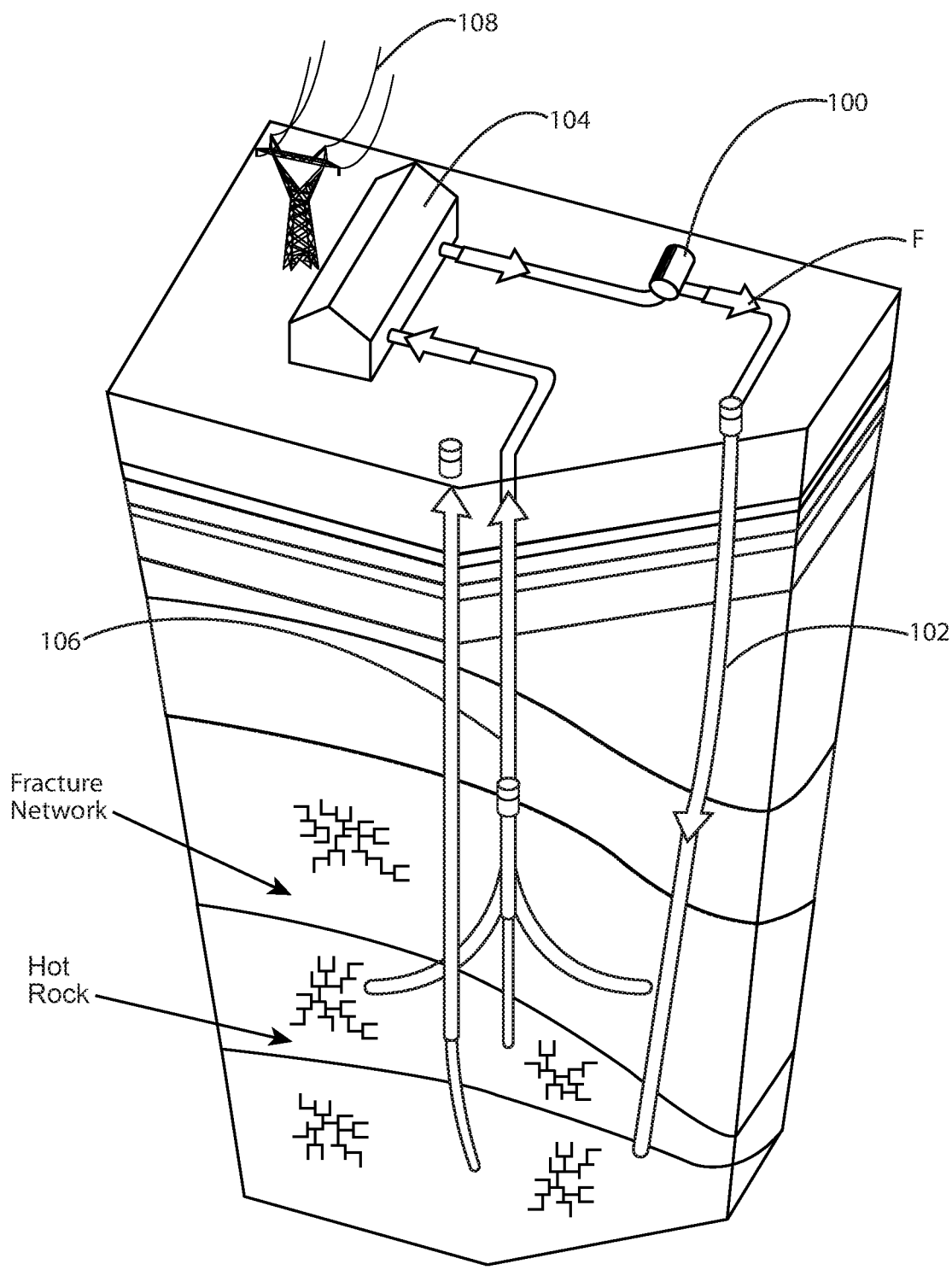
FIG. 1 is a simplified sectional schematic of a geothermal energy conversion plant.
Figure 2:
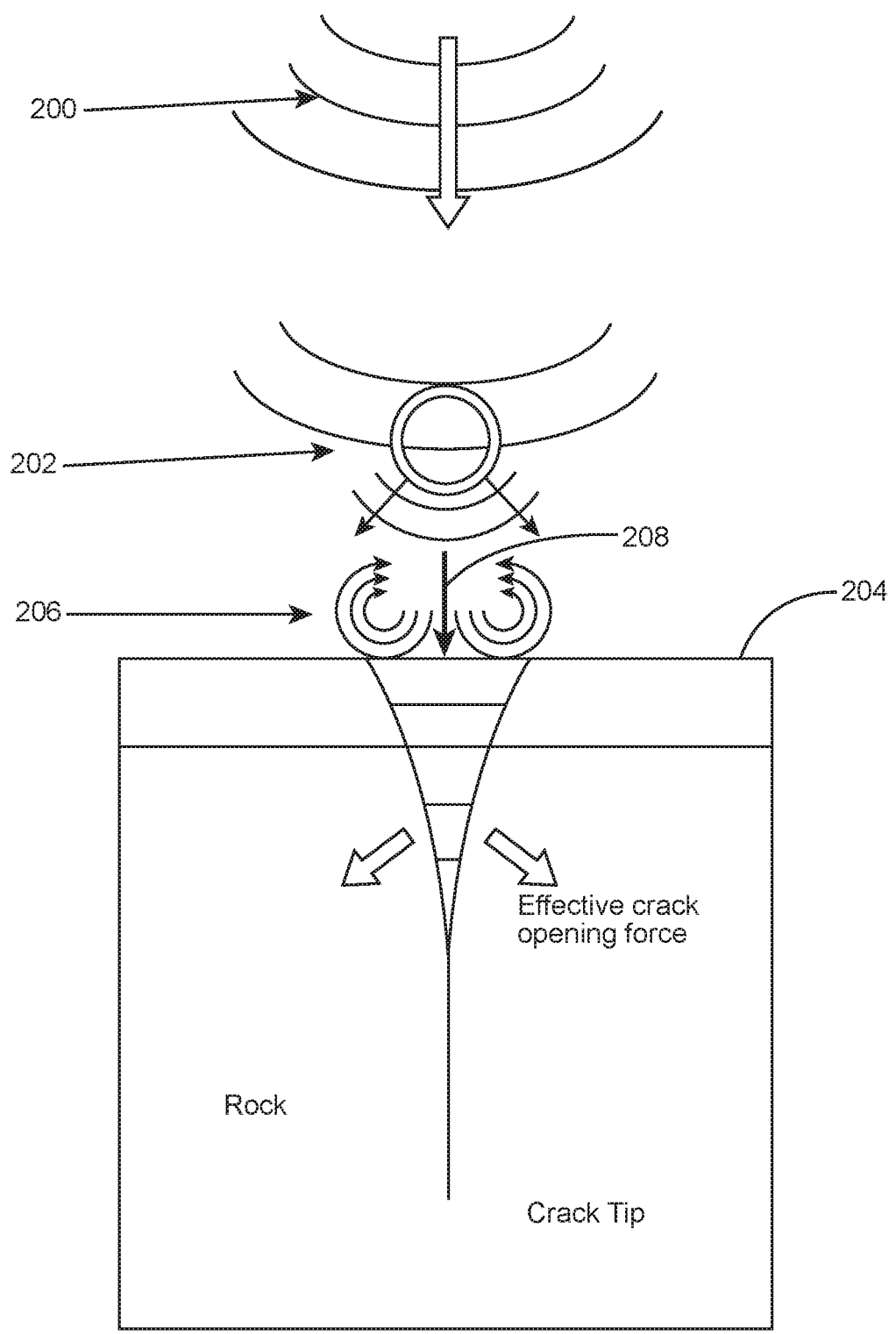
FIG. 2 is a simplified rendition of cavitation mechanics at a fluid and surface interface.
Figure 3:
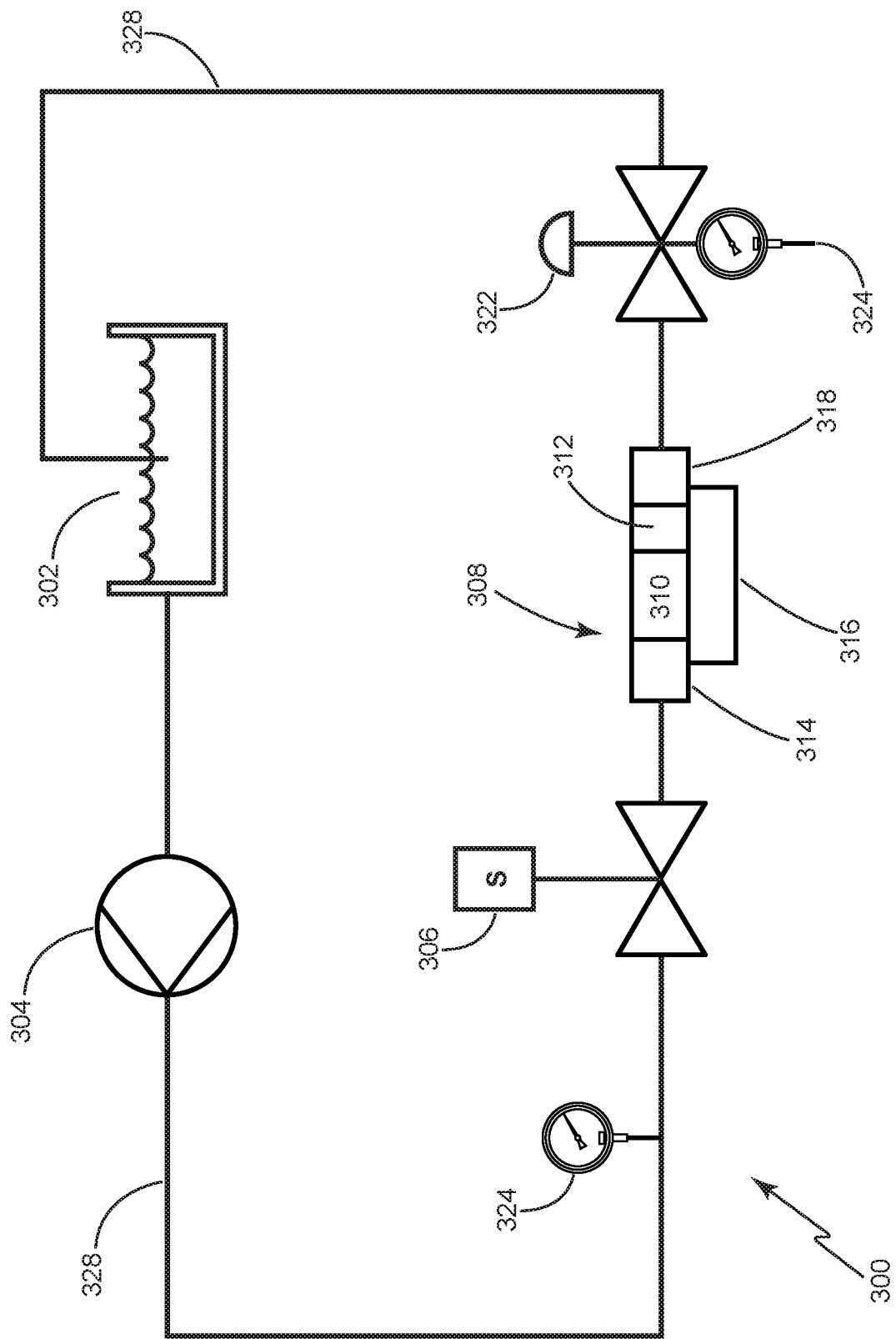
FIG. 3 is a plan view of an exemplary apparatus for simulating a cavitation-based hydro-fracturing of a specimen.

With reference now to FIG. 3, an exemplary apparatus 300 for generating a pulsed pressure induced cavitation technique to simulate the hydrofracturing of a specimen will now be described in greater detail. A working fluid (F), such as water, hydraulic fluid, other fluid, or combination of fluids, is stored in a reservoir 302. The reservoir 302 may be an open or closed vessel and may also include means for filtering, adding, removing, and/or monitoring the level of working fluid (F). A pump 304 draws the working fluid (F) from the upstream reservoir 302 and distributes it to one or more downstream control valves 306 at pressures less than or equal to approximately 300 psi (2068.4 kPa), greater than or equal to approximately 300 psi (2068.4 kPa), or greater than or equal to approximately 300 psi (2068.4 kPa) and less than or equal to approximately 2,000 psi (13789.5 kPa). The pump 304 may operate by compressed air or by an electric motor for example. An air operated liquid piston pump 304 from Haskel International, Inc. Burbank, Calif., 91502 is suitable for this particular application.

The control valve 306 receives the pressurized working fluid (F) from the upstream pump 304 and delivers it to a downstream test chamber 308. High speed compressed air or electric solenoid valves may be used for the control valve 306. A programmable controller (not shown) is used to control the timing frequency of the opening and closing of the control valve 306 to suit each particular simulation. A laptop or desktop computer using LabVIEW software by National Instruments, or a similar controller and software product, may be used. In some examples, the controller may signal the control valve 306 to open and close at a predetermined open and close frequency and/or duration schedule. Frequencies less than or equal to approximately 300 cycles per minute, greater than or equal to approximately 300 cycles per minute, or greater than or equal to approximately 300 and less than or equal to approximately 60,000 cycles per minute may be used. In other examples, the controller may signal the control valve 306 to remain in the open position for a period of time. Although a single control valve 306 is illustrated in FIGS. 3 and 4, two or more control valves 306 may also be used as shown later in FIG. 9.

The exemplary test chamber 308 receives the pressurized working fluid (F) from the upstream control valve 306. In this embodiment, the test chamber 308 is a cylindrical shaped tube defining an internal cavitation chamber 310 for accepting a test specimen 312. This example of a test chamber 308 has an upstream end cap 314 that is fluidly coupled to the upstream control valve 306, a medial body 316 and a downstream end cap 318. The term fluidly coupled refers to a system where the fluid is able to flow between one component and another. At least one of the end caps 314, 318 are removable from the body 316 to allow for loading and unloading of a specimen 312 into the cavitation chamber 310. Corresponding threads 320 on the end caps 314, 318, and body 316 cooperate to provide a fluid seal when assembled together (see FIG. 8). The end caps 314, 318 and body 316 are machined from high-strength, corrosion-resistant material such as stainless steel for example. SAE 304 or SAE 316 stainless steel perform well in this application. Other suitable materials may also be used.

A fluid pressure regulator 322 may be fluidly coupled between the test chamber 308 and the reservoir 302. The pressure regulator 322 may be a diaphragm type, for example, and may contain an integral pressure gauge 324 for ensuring accurate adjustments to the fluid pressure in the system. As is typical in such regulators, a clockwise turn of the adjustment knob increases system pressure and a counterclockwise turn reduces system pressure. One or more pressure gauges 324 may be installed at different locations in the system to ensure proper working fluid (F) pressure.

Figure 4:
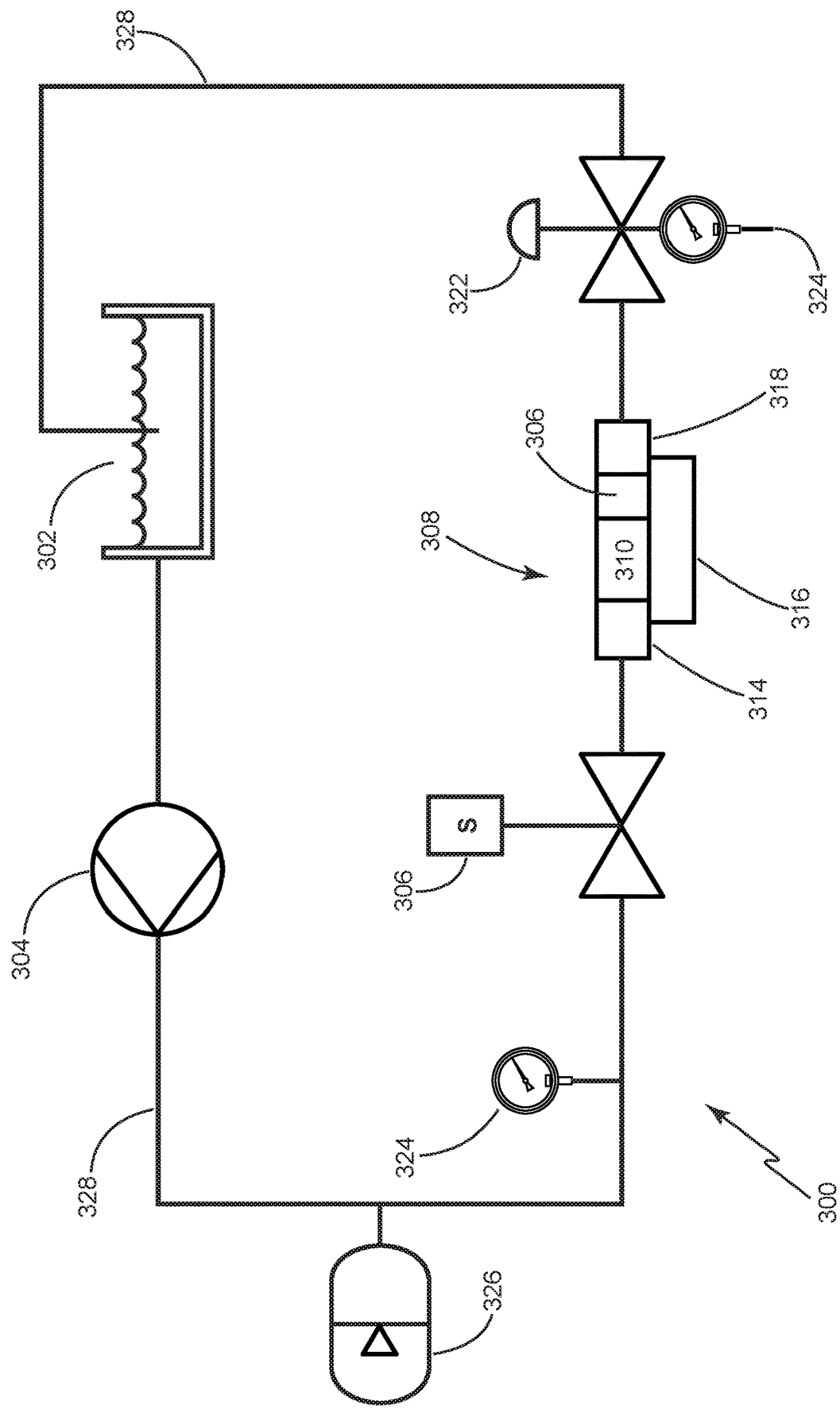
FIG. 4 is an illustration of another exemplary apparatus for simulating a cavitation-based hydro-fracturing of a specimen.
Figure 5:
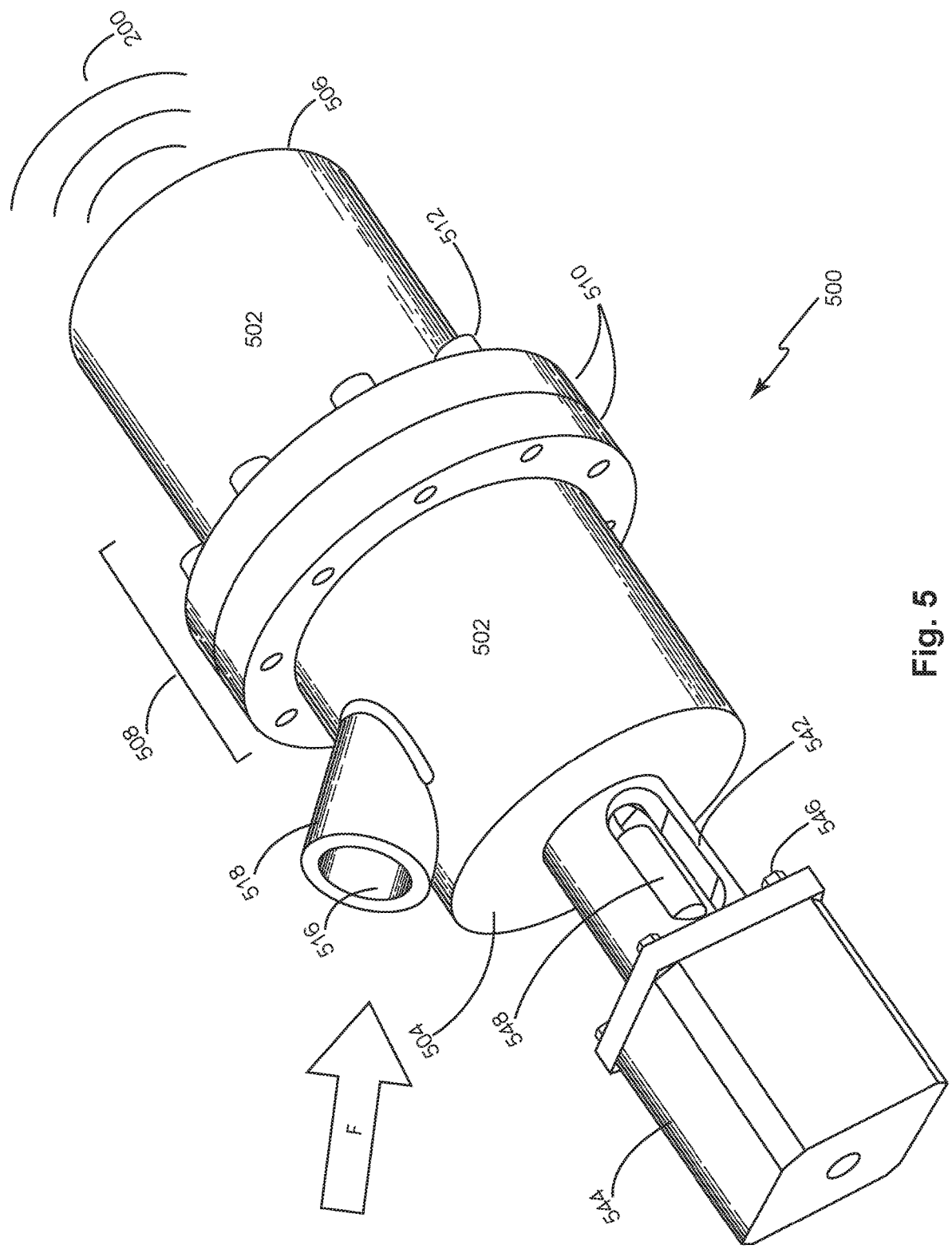
FIG. 5 is an external view of an exemplary control valve for use with the apparatuses of FIGS. 3 and 4.

Referring now to FIG. 4, another exemplary apparatus 300 for generating a pulsed pressure induced cavitation technique to simulate the hydrofracturing of a specimen will now be described in greater detail. In this example, a pressure accumulator 326 may be fluidly coupled between the pump 304 and the control valve 306. The pressure accumulator 326 may be a gas charged type, a bellows type, or other type of pressure accumulator known in the art. The pump 304 delivers the working fluid (F) to the accumulator 326, raising its pressure, until the control valve 306 is opened. All other components and features of this exemplary apparatus 300 are as described above.

Conduits 328 are used to fluidly couple each of the components together and direct the working fluid (F) between components. High pressure capacity conduits 328 made of stainless steel may be used. Suitable couplings such as flared end fittings, or AN style fittings may be used to join the conduits 328 to the individual components described above.

Figure 6:
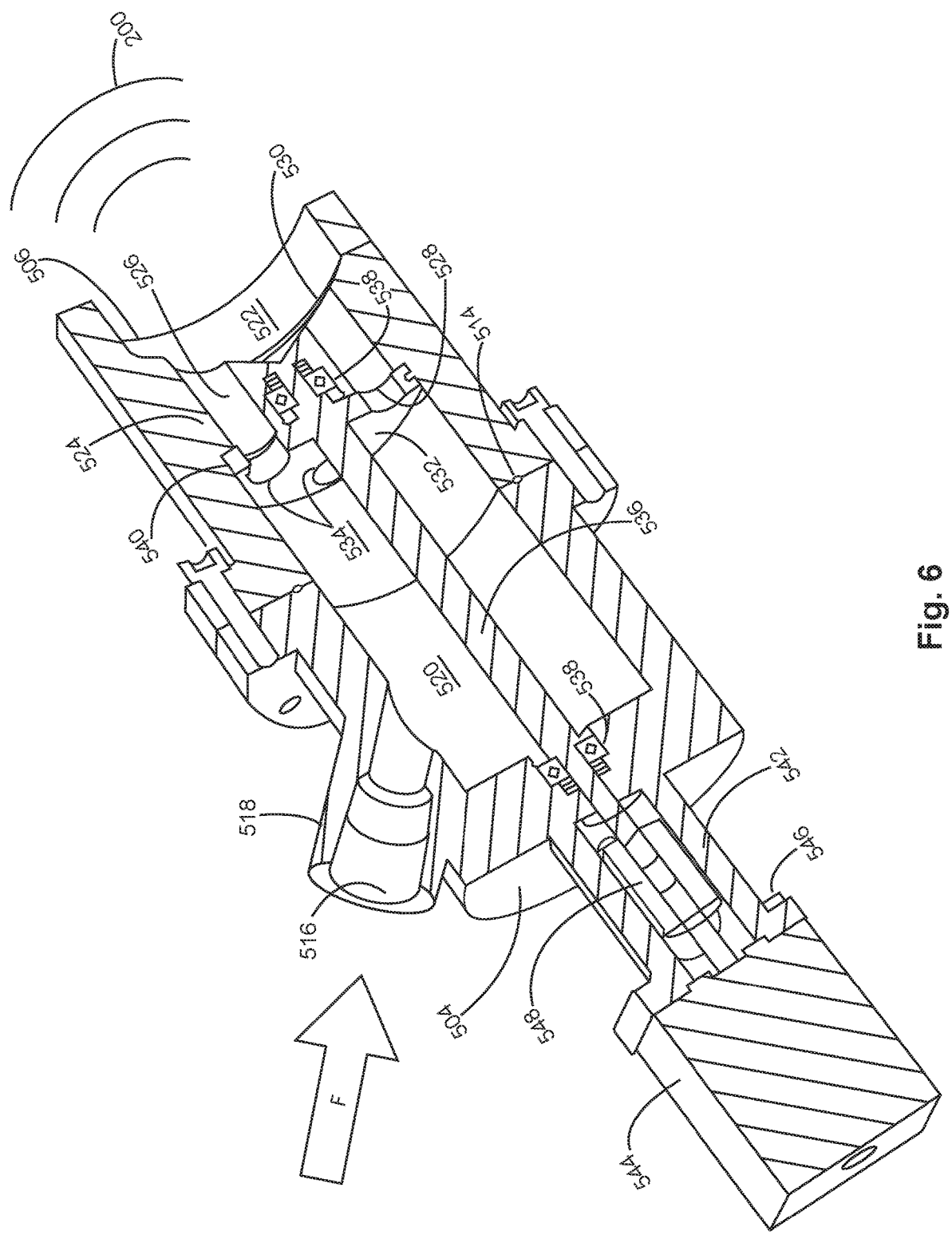
FIG. 6 is a sectional view of the control valve of FIG. 5.
Figure 7:
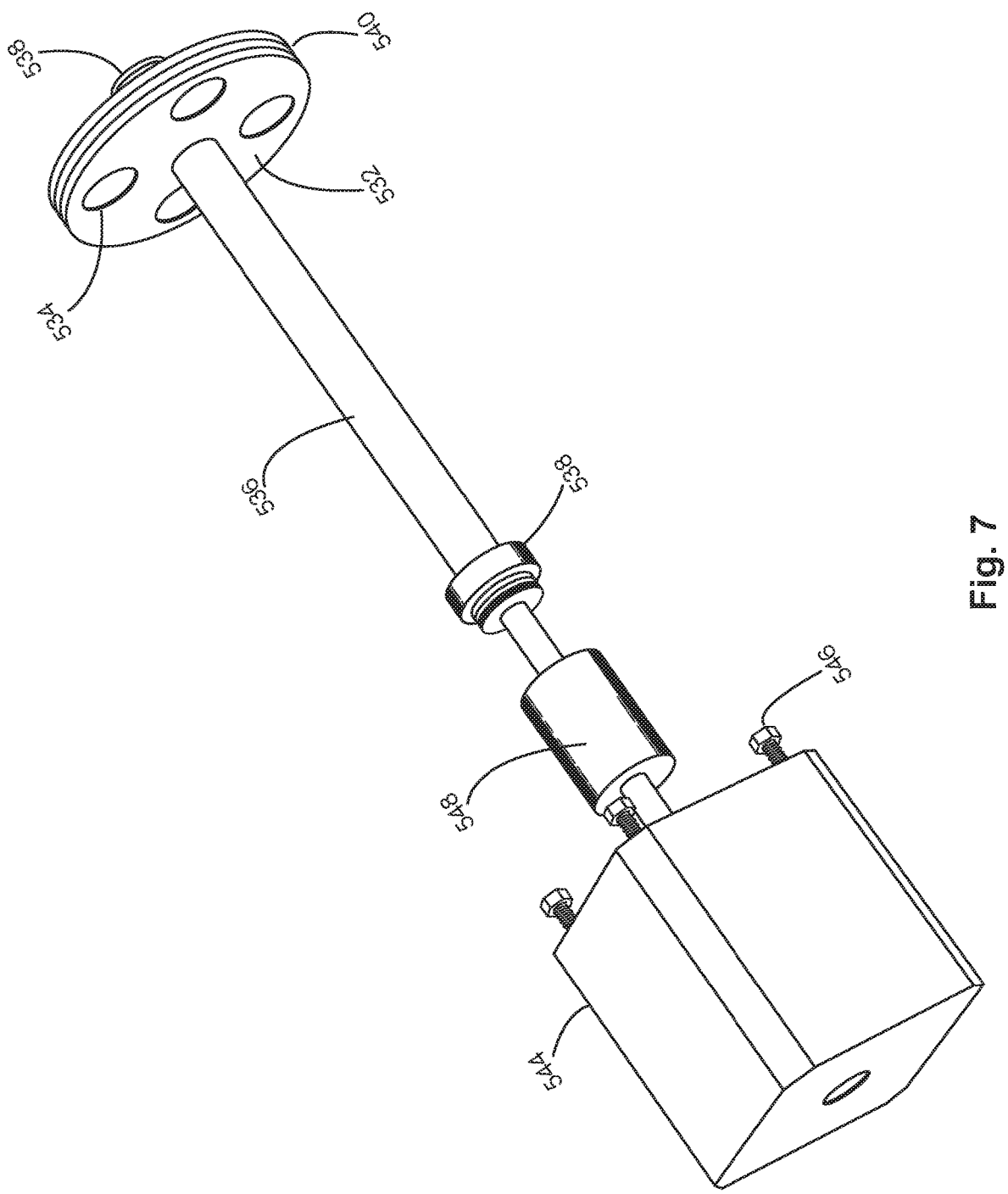
FIG. 7 is an illustration of the internal elements of the control valve of FIG. 5.

Referring now to FIGS. 5-8, another exemplary control valve, also referred to as a rotary shutter valve 500, will be described in greater detail. In this example, an outer housing 502 includes an upstream end 504, an opposite downstream end 506, and a medial portion 508 disposed between the two ends. The outer housing 502 is preferably made from two cylindrical-shaped segments that are joined together at a circumferential flange 510 to simplify assembly, cleaning, inspection, modification, and repair of the valve. The flange 510 is held together with a plurality of circumferentially spaced fasteners 512 such as rivets, clamps or threaded fasteners as shown. An O-ring type seal 514 engages a corresponding gland machined in one or both of the segments as illustrated in FIG. 6. The outer housing 502 is machined from a high strength, high temperature and corrosion resistant material such as stainless steel. SAE 304 or SAE 316 stainless steel performs well in this application.

Figure 8:
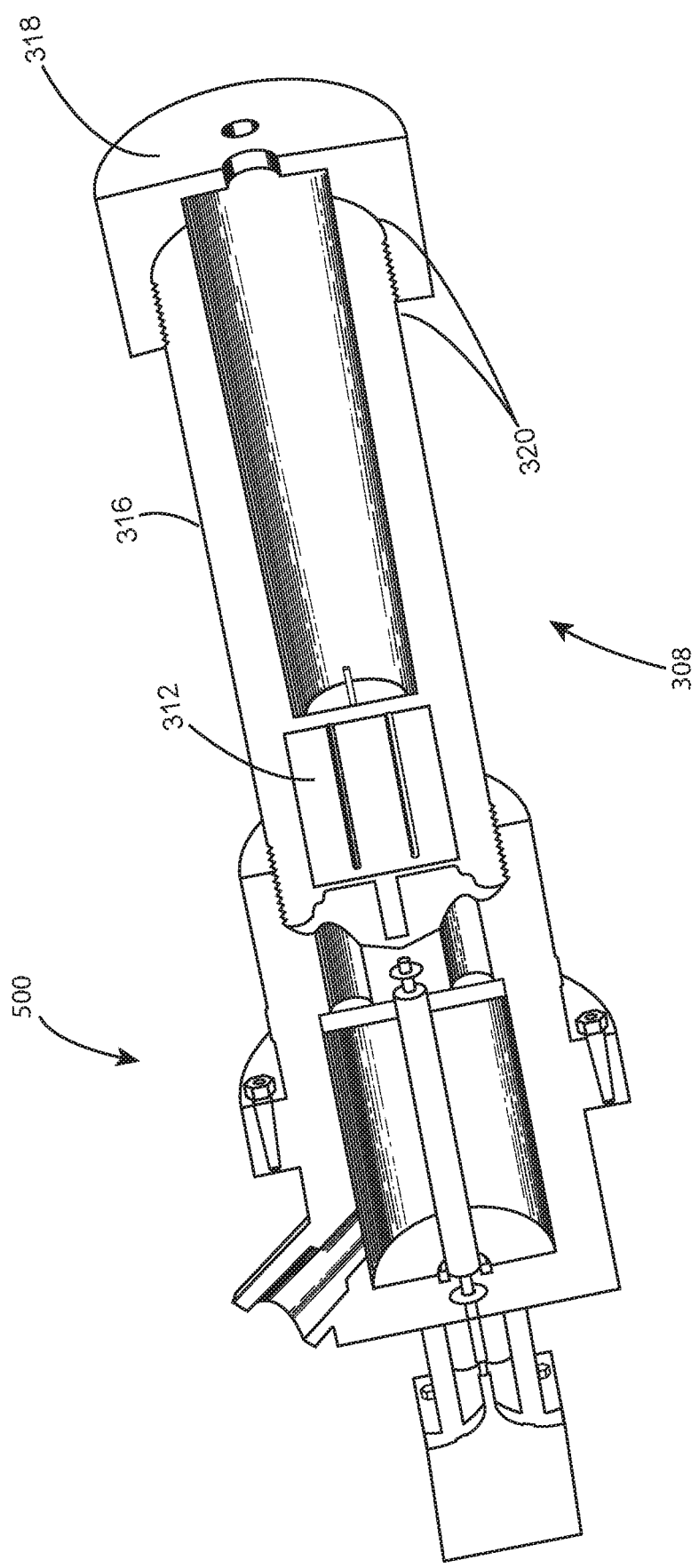
FIG. 8 is a sectional view of a test chamber as used with the control valve of FIG. 5.

An inlet aperture 516 is defined by the outer housing 502 at its upstream end 504. An integral boss 518 provides additional material for connecting a conduit 328 using fittings as described above. The inlet aperture 516 is fluidly coupled to a pressure chamber 520, which is also defined by the outer housing 502 at its upstream end 504. The working fluid (F) flows under pressure from the pump 304, though the conduits 328 to the inlet aperture 516, and into the pressure chamber 520. The downstream end 506 of the outer housing 502 defines a pulse cavity 522, which discharges the pressurized working fluid (F) from the rotary shutter valve 500 as a series of pressure pulses 200 into the test chamber 308 (FIG. 8).

The medial portion 508 of the outer housing 502 defines a bulkhead 524, which separates the pressure chamber 520 from the pulse cavity 522. The bulkhead 524 is preferably made integral with the outer housing 502, but it may also be a separate component that is joined to the outer housing 502 by threads or other mechanical means such as welding. The bulkhead 524 defines one or more bulkhead apertures 526, which fluidly couple the pressure chamber 520 with the pulse cavity 522. In the example shown, two, equally spaced, circular bulkhead apertures 526 are used. In other examples, more or less apertures 526 of circular or other shapes are used. Also, apertures 526 with constant (shown), converging, or diverging cross sections from their upstream to downstream ends are contemplated. The upstream surface 528 of the bulkhead 524 is planar shaped and the downstream surface 530 is concave conical shaped in the example. The concave conical shape of the downstream surface helps direct the pressure waves 200. Other shapes (e.g., concave spherical, concave parabolic) are contemplated for the bulkhead downstream surface 530 as well.

A rotatable shutter 532 is disposed inside of the pressure chamber 520 and adjacent to the upstream surface 528 of the bulkhead 524. The shutter 532 defines one or more windows 534 that generally conform in size, shape, and radial placement with the bulkhead apertures 526. In the example shown, four, equally spaced, circular windows 534 are used. In other examples, more or less windows 534 of circular or other shapes and sizes are used. The shutter 532 is affixed to, or integral with, a shaft 536 that extends through the pressure chamber 520 and exits the outer housing 502 at its upstream end 504.

Thrust bearings 538 support the shaft 536 and fit in pockets machined in the bulkhead 524 and the upstream end 504 of the outer housing. Shoulders on the shaft 536 engage with the thrust bearings 538 to prevent the shaft 536 from moving axially, thus preventing the shutter 532 from contacting the bulkhead 524, seizing, and/or causing destructive vibrations while rotating. An O-ring type seal 540 engages a corresponding gland machined in the radially outer surface of the shutter 532 and prevents leakage of the working fluid (F) from the gap between the shutter 532 and the outer housing 502. A material such as polyurethane, aluminum, graphite or other strong, high temperature capable material may be used for the O-ring seal 540.

Extending outward from the upstream end 504 of the outer housing 502 is a mounting flange 542 for accepting a powering device 544. The powering device 544 is affixed to the mounting flange 542 with one or more fasteners 546 such as rivets, bolts or screws. In the example shown, an electric motor is used as the powering device 544, but a hydraulic motor, a pneumatic motor, or other such device would also work in this application. Electricity, air, or hydraulic fluid is supplied to the powering device 544 by wires or hoses respectively (not shown).

A coupling 548 connects the powering device 544 to the shaft 536. The coupling 548 may include threads, set screws, shear pins, keys, collets, and/or other connecting means. In order to protect the powering device 544 from damage, the coupling 548 is designed to fail if the shutter 532 and/or shaft 536 break, seize, or become otherwise jammed in the pressure chamber 520 for some reason.

During operation of the rotary shutter valve 500, the powering device 544 transfers rotation to the shaft 536 through the coupling 548. The spinning shaft 536 rotates the shutter 532, causing the windows 534 to alternately align with (unblock) and misalign with (block) the one or more bulkhead apertures 526. The pressurized working fluid (F) in the pressure chamber 520 discontinuously flows through the apertures 526, into the pulse cavity 522, and out of the downstream end 506 as pressure pulses 200. The pressure pulses cause cavitation to occur in the test chamber 308 and, in turn, introduce fractures and micro cracks in a test specimen 312 when a test specimen is installed. It is noted that the pulses 200 are controlled by the number and size of the bulkhead apertures 526, the number and size of shutter windows 534, the rotational speed of the shutter 532, and the pressure of the working fluid (F). The shutter 532 can rotate at speeds less than or equal to approximately 300 revolutions per minute, greater than or equal to approximately 300 revolutions per minute, or greater than or equal to approximately 300 revolutions per minute and less than or equal to approximately 60,000 revolutions per minute (RPM).

In this example, the test chamber 308 receives the pressurized working fluid (F) directly from the pulse cavity 522 of the rotary shutter valve 500. The test chamber 308 is a cylindrical shaped tube defining an internal cavitation chamber 310 for accepting a test specimen 312. This example has a medial body 316 and a downstream end cap 318. The test chamber 308 is attached to the distal end 506 with threads or other features to allow for loading and unloading of the specimen 312. Other features of the present test chamber 308 are as described in the earlier examples.

Figure 9:
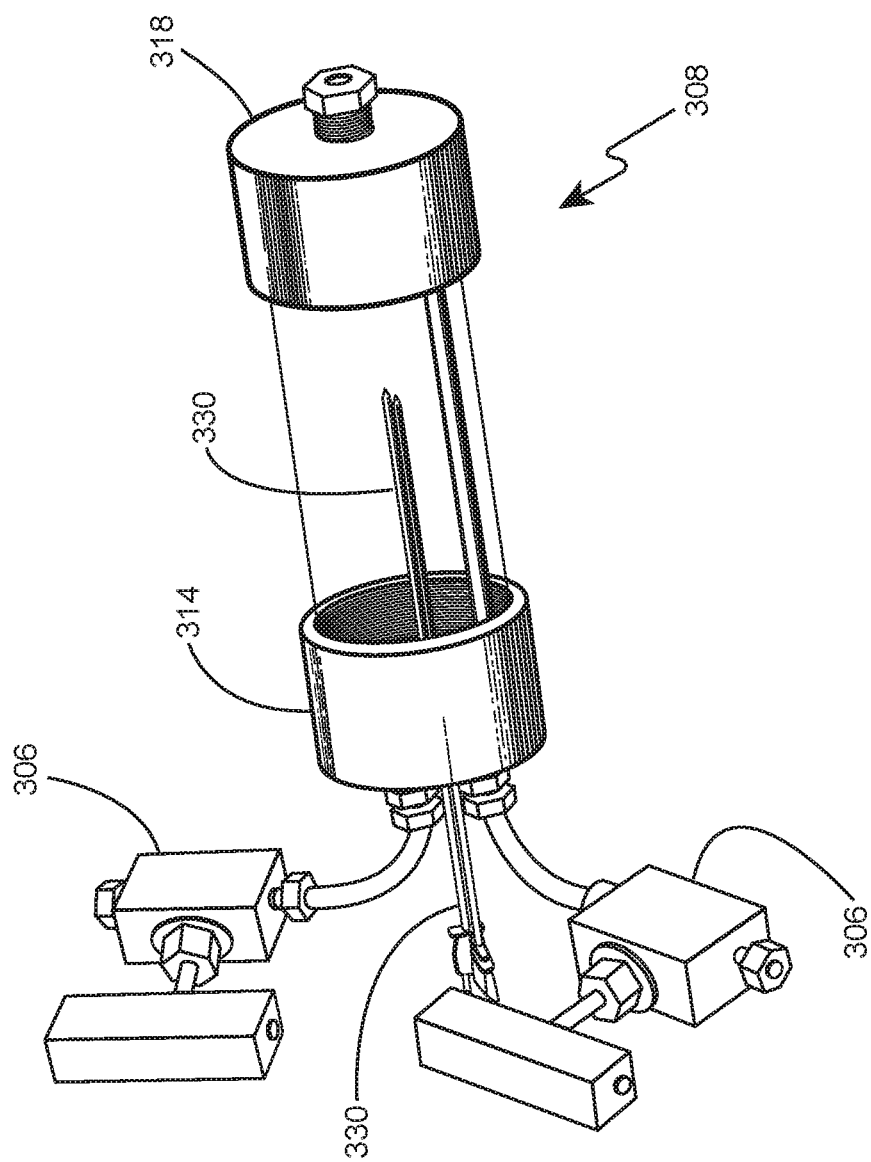
FIG. 9 is an illustration of an exemplary test chamber with instrumentation and dual control valves installed.

FIG. 9 shows another example of a test chamber 308 including instruments 330 for monitoring the conditions inside the cavitation chamber 310 such as the temperature, pressure and flow rate of the working fluid (F). It is also noted that, in this particular embodiment, two control valves 306 are fluidly coupled to the test chamber 308 at the upstream end cap 314 with each valve 306 functioning as described above with respect to FIGS. 3 and 4. In this example, the working fluid (F) pressure pulses entering the test chamber 308 are directly controlled by the frequency and/or duration schedule(s) of the control valve(s), which may be programmed to open and close according to the same schedule or according to different schedules.

Figure 10:
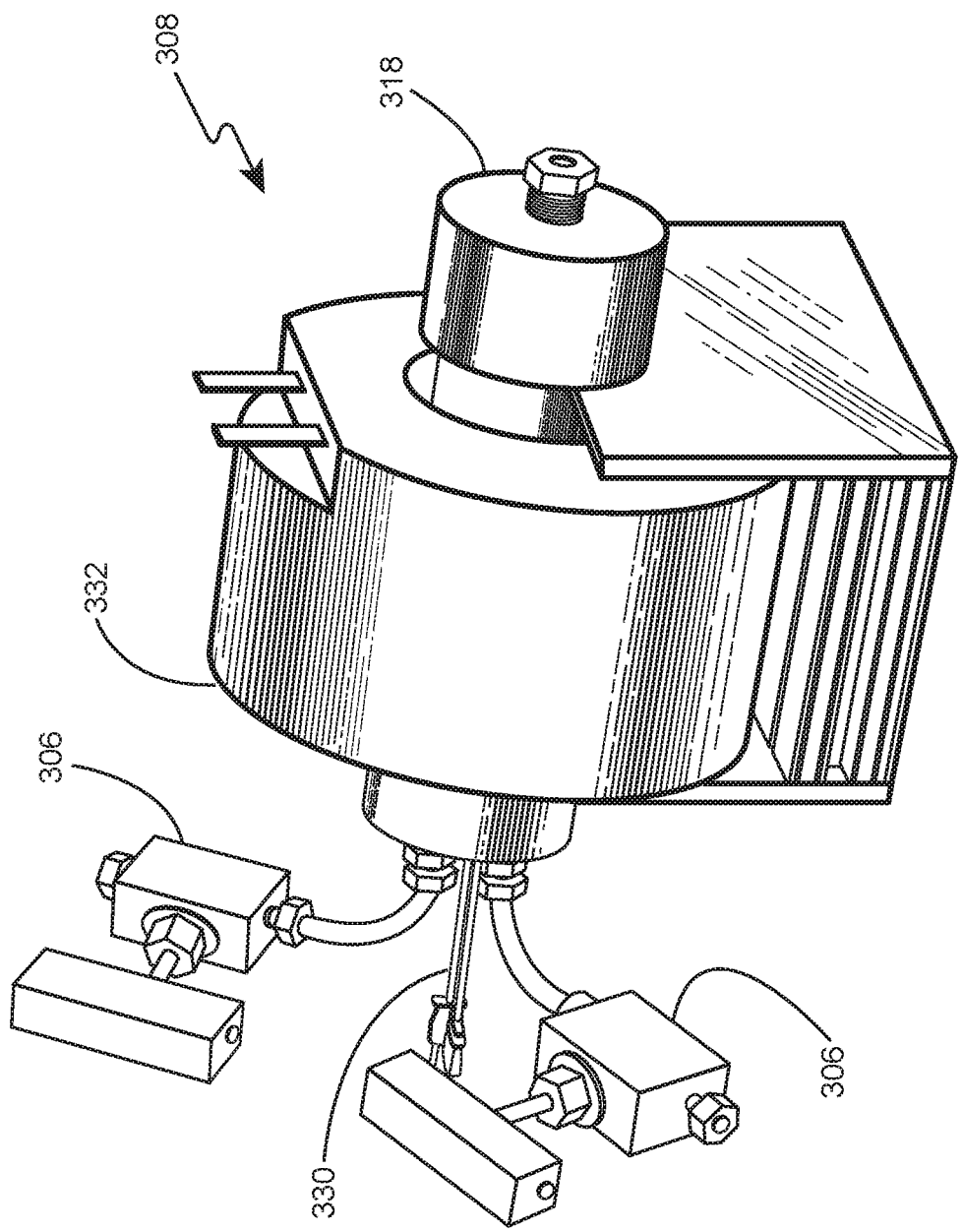
FIG. 10 is an illustration of an exemplary heating device for use with the test chambers.

Referring now to the example of FIG. 10, the test chamber 308 may be surrounded, at least partially, by a heating element 332 to simulate the elevated temperature found in a EGS reservoir, or an oil or gas well. In the example shown, a resistance heater 332 completely surrounds the test chamber 308, but in other examples only a portion of the chamber is surrounded by a heater. In some examples, the heater is able to raise the temperature of the test chamber 308 and specimen 312 to a temperature less than or equal to approximately 50 degrees Celsius (122 Fahrenheit), greater than or equal to approximately 50 degrees Celsius (122 Fahrenheit), or greater than or equal to approximately 50 degrees Celsius (122 Fahrenheit) and less than or equal to approximately 250 degrees Celsius (482 Fahrenheit).

Referring lastly to FIGS. 11 and 12, exemplary specimens 312 for evaluating pressure pulse cavitation in EGS, oil or gas well rock formations are shown. The specimens 312 are generally cylindrical in shape and defined by a circular top surface 334, a circular bottom surface 336 and a convex side surface 338 extending between the top and bottom surfaces 334, 336. The specimens 312 are comprised of rock or stone material from larger rock specimens of the type found in EGS reservoirs, oil or gas wells. They are machined or core drilled to shape and sized to fit within the test chamber 308.

In the example of FIG. 11, a blind hole 340 mimics a stimulation well. During testing, the hole 340 is filled with working fluid (F) and is subject to cavitation by controlling the opening frequency and duration of the control valve(s). In the example of FIG. 12, a series of artificial flaws 342 are included in the side surface 338. Here, artificial flaws 342 such as cracks or fissures are introduced into the side surface 342 with a band saw, a water jet or other cutting device to simulate an existing crack structure and/or to assist the initiation of crack stimulation.

In the examples of FIGS. 13-15, a shell body 344 is defined by a generally circular top surface 334, a circular bottom surface 336 and a convex side surface 338 joining the top and bottom surfaces 334, 336. An aperture 346, having an interior surface 348, is disposed through the shell body 344 and is defined by a circular opening in the top and bottom surfaces 334, 336. A separate, core body 350 is defined by a circular top surface 334, a circular bottom surface 336 and a convex side surface 338 joining the top and bottom surfaces 334, 336. The aperture 346 of the shell 344 is sized to accept the core 350 therein. As in the previous examples, the specimens 312 are comprised of rock or stone material of the type found in EGS reservoirs, oil or gas wells. They are machined or core drilled to shape and sized to fit within the test chamber 308.

In the present examples, artificial flaws 342 (surface flaws or through thickness flaws) may be introduced into one or both of the shell 344 and core 350. During testing, cavitating working fluid (F) is forced to flow along the interface between the shell 344 and the core 350. Furthermore, by incorporating a 45 degree pitch spiral notch to the side surface 338 of the core 350 and/or a spiral through thickness notch to the side surface 338 of the shell 344, these specimens 312 can also be used to evaluate the fracture toughness degradation during the EGS reservoir operation.

Further information about a spiral-notch torsion test system (SNTT) may be found in U.S. Pat. No. 6,588,283, "Fracture Toughness Determination Using Spiral-Grooved Cylindrical Specimen and Pure Torsional Loading", to Jy-An Wang and Kenneth C. Liu, the disclosure of which is hereby incorporated by reference. Additional information may also be found in "A New Test Method for Determining the Fracture Toughness of Concrete Materials" by J. A. Wang, K. C. Liu, D. N. in Cement and Concrete Research, Volume 40, Issue 3, March 2010, Pages 497-499, K. Scrivener editor. Such benchmark data can further provide the guideline on the stimulation pressure pulse design parameters and their effectiveness for generating crack growth.

After simulation testing, the specimens 312 are examined in order to evaluate the fracture network caused by the pressure pulse cavitation technique by the apparatus 300. It was found that two main mechanisms occur in cavitation erosion damage: high pressure shock waves created by the collapsing vapor bubbles, which can result in material fatigue and plastic deformation; and micro-jet impingement resulting in asymmetrical collapse of the vapor bubble near the specimen 312 surface. It was also found that when the bubbles collapse due to external pressure, the working fluid (F) is accelerated toward the center of the bubble. Bubbles formed near solid surfaces have the largest potential to cause micro cracking of the specimen 312 surface.

While this disclosure describes and enables several examples of a simulator apparatuses and methods for researching geothermal reservoir stimulation, other examples and applications are contemplated. Accordingly, the invention is intended to embrace those alternatives, modifications, equivalents, and variations as fall within the broad scope of the appended claims. The technology disclosed and claimed herein may be available for licensing in specific fields of use by the assignee of record.

What is claimed is:

1. A test specimen comprising:
    a shell body, said shell body being defined by a circular top surface, a circular bottom surface, and a convex exterior side surface joining the top surface of said shell body and the bottom surface of said shell body;
    an aperture disposed through said shell body and defined by an interior side surface, an opening in the top surface, and an opening in the bottom surface;
    a core body defined by a top surface, a bottom surface and a convex exterior side surface joining the top surface of said core body and the bottom surface of said core body, wherein said core body is disposed inside of the aperture in said shell body and said shell body and said core body are each made of naturally hardened rock, and wherein the interior side surface of said shell body and the exterior side surface of said core body are opposite each other to define an interface therebetween; and a pressurized working fluid within the interface between the interior side surface of said shell body and the exterior side surface of said core body to generate pulsed pressure induced cavitation therein in order to evaluate the fracture toughness of said shell body or said core body.

2. The test specimen of claim 1 and further comprising: a 45-degree pitch spiral notch type of an artificial flaw in the side surface of said core body.

3. The test specimen of claim 2 and further comprising: a 45-degree pitch spiral notch type of an artificial flaw through the thickness of said shell body.

4. The test specimen of claim 1 wherein the aperture in said shell body is sized to accept said core body and to allow the working fluid to flow through the interface between said shell body and said core body.

5. The test specimen of claim 1 wherein at least one of said shell body and said core body includes an artificial flaw.

6. The test specimen of claim 5 wherein said core body includes a blind hole in the top surface to mimic a stimulation well.

7. The test specimen of claim 5 wherein said core body includes a crack or fissure type of an artificial flaw in the side surface.

8. A rock specimen comprising:
a specimen body that is cylindrical in shape, said body being made of naturally hardened rock and defined by a top surface, a bottom surface and a convex exterior side surface joining the top surface and the bottom surface; and wherein a surface of said body includes an artificial flaw and the surface being configured to be exposed to a pulsed pressure induced cavitation from a working fluid in order to evaluate the fracture toughness of the specimen.

9. The rock specimen of claim 8 wherein the surface is the top surface and the top surface further includes an unthreaded blind hole.

10. The rock specimen of claim 8 wherein the surface is the convex exterior side surface and the artificial flaw is a crack or a fissure.

* * * * *